United States Patent
Planman et al.

(10) Patent No.: US 9,375,177 B2
(45) Date of Patent: Jun. 28, 2016

(54) HEALTH MONITORING DEVICE, DEVICE MODULES AND METHOD

(75) Inventors: Jukka Planman, Helsinki (FI); Tuomas Planman, Espoo (FI)

(73) Assignee: IHQ Innovation Headquarters Oy, Helsinki (FI)

( * ) Notice: Subject to any disclaimer, the term of this patent is extended or adjusted under 35 U.S.C. 154(b) by 0 days.

(21) Appl. No.: 13/299,946

(22) Filed: Nov. 18, 2011

(65) Prior Publication Data

US 2012/0065544 A1 Mar. 15, 2012

Related U.S. Application Data

(62) Division of application No. 11/996,232, filed as application No. PCT/FI2006/000261 on Jul. 19, 2006, now Pat. No. 8,062,235.

(30) Foreign Application Priority Data

Jul. 19, 2005 (FI) ...................................... 20050768

(51) Int. Cl.
*A61B 5/145* (2006.01)
*A61B 5/151* (2006.01)
*A61B 5/157* (2006.01)
*A61B 5/15* (2006.01)

(52) U.S. Cl.
CPC ............... *A61B 5/157* (2013.01); *A61B 5/1411* (2013.01); *A61B 5/14532* (2013.01); *A61B 5/15186* (2013.01); *A61B 2562/0295* (2013.01)

(58) Field of Classification Search
USPC ............................ 600/583, 584; 606/181, 182
See application file for complete search history.

(56) References Cited

U.S. PATENT DOCUMENTS

| 4,790,979 | A | 12/1988 | Terminiello et al. |
| 6,027,459 | A | 2/2000 | Shain et al. |

(Continued)

FOREIGN PATENT DOCUMENTS

| DE | 103 32 488 A1 | 2/2005 |
| DE | 603 10 160 T2 | 9/2007 |

(Continued)

OTHER PUBLICATIONS

Roche Diagnostics GmbH, Accu-Chek Compact Owner's Manual, pp. 2-99. www.accu-chek.com.

(Continued)

*Primary Examiner* — Sean Dougherty
(74) *Attorney, Agent, or Firm* — McCormick, Paulding & Huber LLP

(57) ABSTRACT

The present invention relates to a health monitoring device for measuring blood or tissue indicators and a strip cassette. The device comprises a body having first and second openings, a piercing means being connected to the body and having a piercing head, the piercing means being arranged to extend from the first opening and cockable and releasable for piercing the skin with the piercing head, and a space into which a number of sensor strips can be arranged so that the strips can be brought out from the body one at a time. The device further comprises a shutter that is functionally connected to the body and has a first position arranged to tightly close the first and second openings, and a second position for allowing one sensor strip to be pushed from the first opening into sampling position and for exposing the first and second openings.

14 Claims, 14 Drawing Sheets

(56) References Cited

U.S. PATENT DOCUMENTS

| | | | |
|---|---|---|---|
| 6,837,858 B2 * | 1/2005 | Cunningham et al. | 600/573 |
| 2002/0188224 A1 | 12/2002 | Roe et al. | |
| 2003/0195435 A1 * | 10/2003 | Williams | 600/583 |
| 2003/0212345 A1 | 11/2003 | McAllister et al. | |
| 2004/0267300 A1 | 12/2004 | Mace | |
| 2006/0189895 A1 * | 8/2006 | Neel et al. | 600/584 |

FOREIGN PATENT DOCUMENTS

| | | |
|---|---|---|
| EP | 0449525 A1 | 10/1991 |
| EP | 1485021 B1 | 12/2004 |
| EP | 1488736 A1 | 12/2004 |
| JP | 2000152923 A | 6/2000 |
| JP | 2002200061 A | 7/2002 |
| WO | 03070099 A1 | 8/2003 |
| WO | 03082091 A2 | 10/2003 |
| WO | 03083469 A2 | 10/2003 |
| WO | 2005018710 A2 | 3/2005 |
| WO | 2005018711 A2 | 3/2005 |
| WO | 2005034740 A2 | 4/2005 |

OTHER PUBLICATIONS

Photographs of Accu-Chek monitor.
Japanese Office Action dated Dec. 16, 2011.
Japanese Office Action dated May 2, 2012.

* cited by examiner

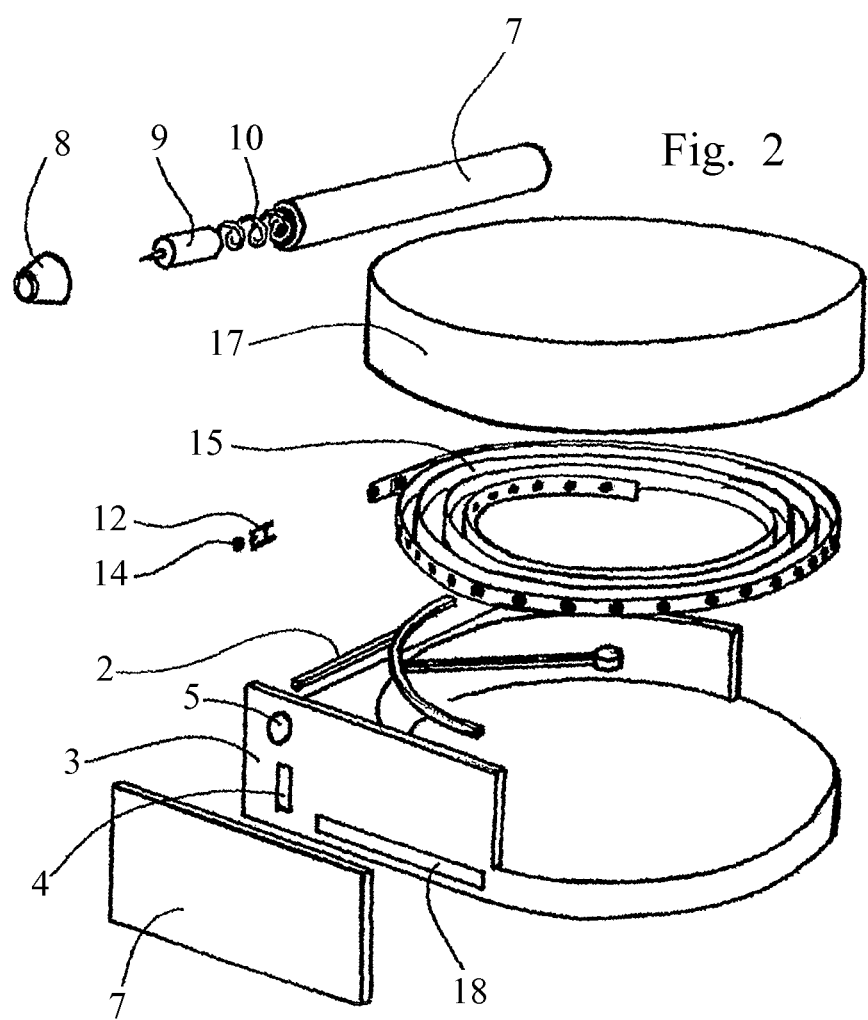

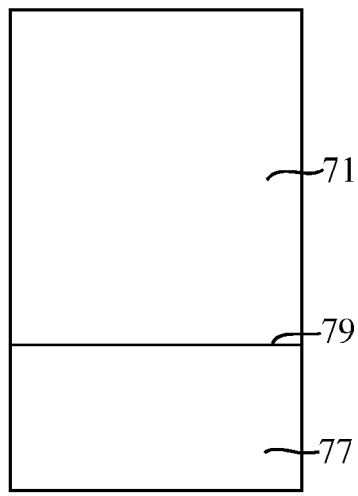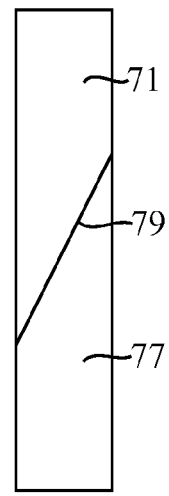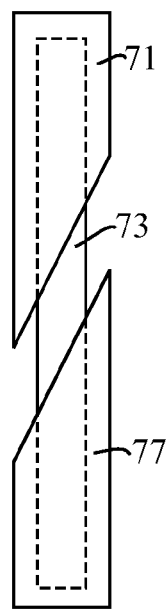
Fig. 7a  Fig. 7b  Fig. 7d
Fig. 7c
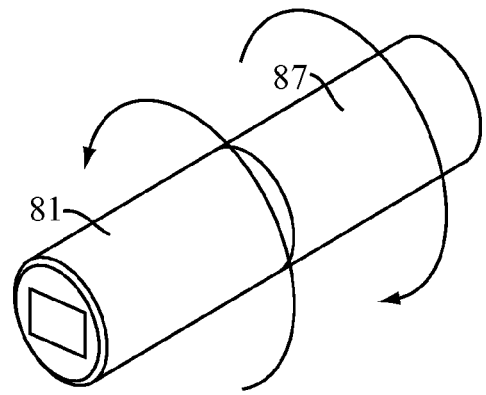
Fig. 8a
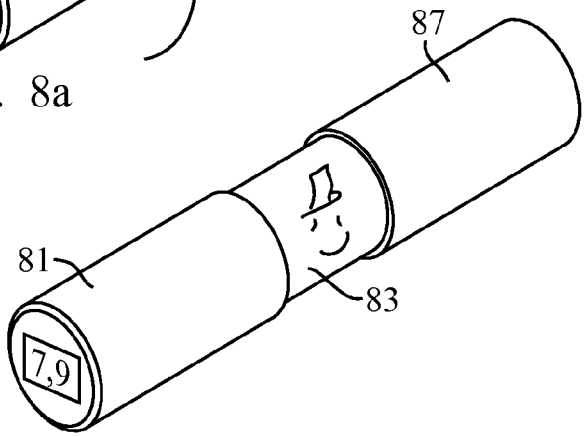
Fig. 8b

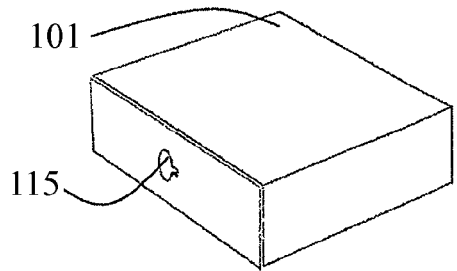
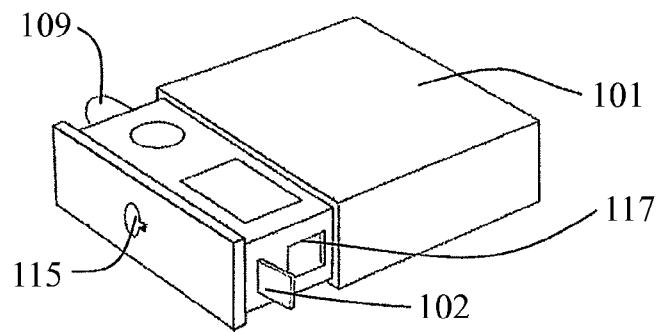
Fig. 10a    Fig. 10b
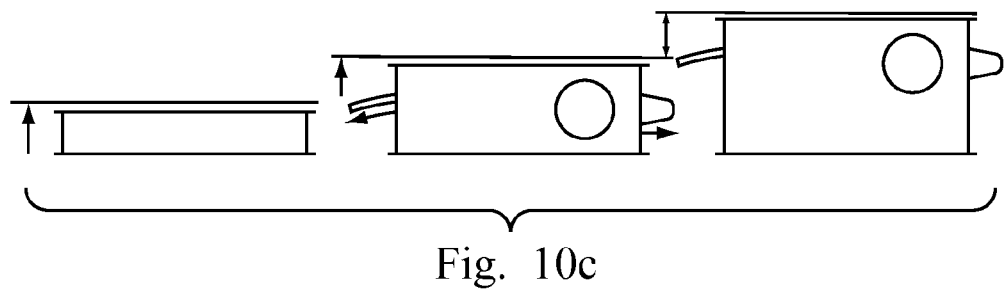
Fig. 10c
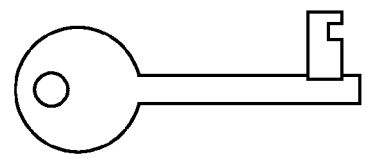
Fig. 10d

HEALTH MONITORING DEVICE, DEVICE MODULES AND METHOD

CROSS REFERENCE TO RELATED APPLICATIONS

This application is a divisional application of U.S. patent application Ser. No. 11/996,232, filed on Jan. 31, 2008, which claims priority to International Application No. PCT/FI2006/000261, filed on Jul. 19, 2006, which further claims priority to Finland Patent Application No. 20050768, filed on Jul. 19, 2005. The contents of each of these applications are incorporated by reference herein in their entireties.

FIELD OF THE INVENTION

The present invention relates to a health monitoring device for measuring blood indicators. Such a device comprises a lancet for piercing the skin for bringing out blood and it includes readiness for a number of disposable sensor strips used for analysing the blood sample. The invention further relates to a device module to be attached to the health monitoring device, the module comprising a number of sensor strips.

BACKGROUND OF THE INVENTION

Currently there are over 120 million diabetics world-wide. By 2025 the number is estimated to be already about 300 million. For example, in Finland about 4 percent of the population have diabetes. Diabetes is divided into juvenile diabetes (Type I) and adult onset diabetes (Type II).

Diabetes has a heavy effect on the everyday life of a diabetic. Especially persons with juvenile diabetes must, in order to maintain sugar balance, in addition to constantly monitoring their diet take care that their insulin intake corresponds to their diet and consumption. Should there be deviations between the amount of sugar consumed with food and the amount of insulin intake, the blood sugar values of a diabetic can vary on a wide scale, as the body can't use the sugar. A constantly too high a sugar value can lead to, for example, accumulation of sugar in the fats and proteins of the body, which can cause organic changes in, for example, eyes, kidneys and nerves as well as in heart and blood circulation. In an insulin shock, on the other hand, the glucose content of blood drops to a very low level and the person can become unconscious. In order to avoid these drawbacks, it is recommended that diabetics constantly monitor their blood sugar, many times per day.

A number portable devices have been developed for measuring blood sugar content. What is traditionally used is a separate needle pen by means of which the skin is pierced, a sensor strip on which the blood sample is placed and a separate measurement device. The individually packed strip is manually placed in the opening in the meter. Such a measurement device is difficult to transport and use. A relatively large carrying pouch is needed, from which the various elements must be taken out and used in a multi-step measurement operation. According to a survey (United States Food and Drug Administration, FDA, http://www.fda.gov/diabetes/glucose.html) users do not feel taking the blood sample is a problem, but instead the need for a number of components and the fact that such a measurement is difficult to carry out unnoticed by others, are felt to be problems by the users.

Meters with sensor strips stored in an internal magazine in the device, from which the strip is taken out for the measurement, have also been developed. Strip magazines are disclosed in, e.g. U.S. Pat. Nos. 5,575,403, 5,510,266 and 5,489,414.

Strips arranged as belts are shown in U.S. Pat. No. 4,218,421 and European patent 1360935. In the former, a number of strips arranged next to each other are transported one after the other in a roll to roll method, and in the latter the strips include both a needle element and a meter element. In the latter, the strip is protected by a protective layer that is removed from the belt of strips when the strip is removed from the device. The strip belt itself is returned to a roll inside the device.

Published application WO 03/83469 discloses a pistol-like device with a lancet device arranged thereto and a number of test strips in stack form. The lancet device can be cocked by means of a switch arranged on the side of the device and the strips can be pushed from the device one at a time. The end of the lancet can be protected by a cap that can be removed from the device. The device also comprises measurement electronics and a display for showing the results of the analysis.

The published US application 2003/191415 discloses a device bringing the strip automatically to the blood sample, the drawing of which can be amended with vacuum. A separate lever is installed in the housing of the device for preparing the device for use.

The published US application 2004/003903 and WO publication 03/071940 disclose wristwatch-like devices containing a number of lancets and sensor elements arranged radially. A lancet corresponds to each sensor. As the measurement devices are personal and typically one needle of a lancet can be used many times, it is difficult to reason the use of multiple lancets. Manufacturing such a device will inevitably be expensive and its structure is complex. Additionally, especially in case of the former application, hygienic problems are a drawback, because as the finger is pressed directly against the device, the blood sample can easily be in contact with the outer surface of the device.

A mobile phone (LG KP8400) having an opening in the side for a test strip used for measuring blood sugar is known. The electronics of the phone are used in analysing the strip. The device does not contain a lancet device.

DE publication 19819407 and WO publication 2005/032372 disclose twin-hub cassettes in which the sensor strip can be transported from one hub to the other. A new sensor area is exposed by pulling so that a blood sample can be applied thereto. Such cassettes are inevitably rather large and so they can not be used in very small health monitoring devices. In the use of such devices, transporting the used strip back to the device and storing it is unhygienic and unpleasant. Blood can also stain the inner surface of the device in the used strips' compartment. A continuous strip does not allow separating unused strips from used ones, either. Such a separation is necessary, as the enzymes of normal strips are deteriorated by the influence of oxygen and moisture.

In the above-mentioned prior art solutions the exit opening of the strip and/or the lancet is unprotected. Thus, the meter must be kept in, for example, a pouch or a case for preventing soiling and accumulation of dust of the strip opening and/or the lancet. Separate strips are hermetically packed, usually individually or in a sealed box. The strip cassettes can also tightly enclose the strips, but even in this case dirt can get into the device from the opening of the strip and the lancet. Known devices are also relatively large. However, as this is a case of daily health monitoring carried out many times per day, there is a need for small, simple and reliable devices, the use of which does not draw attention.

SUMMARY OF THE INVENTION

The object of the invention is to produce a health monitoring device allowing the measurement of blood indicators in a more simple and less conspicuous way than with prior art devices.

Another object of the invention is to produce a new sensor strip cassette suitable for use in a health monitoring device according to the invention.

The invention is based on the idea that the device comprises an openable shutter which, when closed, tightly covers both the exit opening of the lancet and the exit opening of the sensor strip. When the shutter is opened, the openings of the lancet and the sensor strip are exposed, whereby the piercing head of the lancet device can be pushed from the opening of the lancet for piercing the skin and the measurement area of the strip can be pushed from the opening of the sensor strip.

According to one preferable embodiment the shutter is functionally connected to the lancet device. The lancet device is especially preferably cocked and/or the sensor strip pushed out from its opening with the same movement that is used for opening the shutter. Thus, the device is ready for use after the opening of the shutter. The force needed for cocking and pushing out can be accomplished by the opening movement of the shutter. Such a device thus comprises a body having openings for the piercing head (first opening) of the piercing means (lancet device) and the sensor strip (second opening). The piercing means is arranged in the device so that its piercing head (lancet) can be pushed from the first opening of the body. The piercing means can also be cocked into stand-by state and further released into rest position for piercing the skin. Typically the device also comprises a cavity at least partly limited by the body for a number of sensor strips that can be arranged adjacent the second opening so that they can be brought away from the device one at a time through the second opening. The shutter is arranged in the device so that in the first position it protects the first and second openings and can be brought to second position for cocking the piercing means and for bringing one sensor strip into measurement position so that the first and second openings are simultaneously exposed.

The lancet can be released for piercing the skin and further for bringing out blood by means of a shutter or a separate releasing device. After releasing the lancet the drop of blood can be conveyed to the measurement area of the sensor strip, the measurement result can be transferred to the electronics, the sensor can be removed from the device and the shutter can be closed. Thus the device is again in its basic state.

By piercing means we generally mean a device having a lancet and other means as well as a mechanism by means of which it can be used for piercing the skin. For piercing the skin, the lancet is pushed out through the first opening of the device for a short time. Typically the mechanism used is a manually cockable and releasable spring-operated mechanism that can be cocked into stand-by state and then released into rest position for piercing the skin. Other possible mechanisms include, among others, electrically operated needle devices. Typically the piercing head of the piercing means can be manually changed. By a piercing means we mean multi-pointed lancet magazines and devices shown in publications of the art. In such solutions a new, unused needle can be automatically brought up for each piercing of the skin. It will be obvious to one skilled in the art that needles can be arranged inside the device in many ways so that can be individually positioned for operation and can be subsequently removed or stored inside the device.

A cassette according to the invention comprises covers and a hub, rotatably attached thereto. A sensor element band is spirally attached to the hub so that the outermost sensor element of the spiral can be pushed out from the cassette when the hub is rotated.

A sensor element arrangement according to the invention comprises a number of disposable sensor strips, each of which comprises a measurement area and contacts attached on the measurement area for analysing the blood arranged on the measurement area. Sensor strips are arranged one after the other in longitudinal direction as a flexible band.

In a method according to the invention for carrying out an at least two-step health monitoring measurement is used a portable health monitoring device, the device comprising a first means for carrying out the first step and a second means for carrying out the second step. The health monitoring device additionally comprises a shutter that in its first position comprises at least the operative parts of the first and second means (i.e. the piercing head and the opening or openings of the sensor strip, for example). The measurement is done by taking the shutter to the second position for exposing the first and second means and for bringing the first, second or both means into the operational position and typically also for switching the device on, using the first and second means while the shutter is in its second position and by bringing the shutter back to its first position.

More specifically, one embodiment of a health monitoring device according to the present invention comprises a body having a first opening and a second opening, a piercing means attached to the body and having a piercing head arranged to extend out from the first opening of the body, the piercing means being cockable and further releasable for piercing the skin with its piercing head, and a space arranged in connection with the body, into which space a number of sensor strips can be arranged so that they can be brought out from the device one by one through the second opening of the body into sampling position, wherein a shutter being arranged to tightly cover in its first position the first and the second opening of the body, the shutter being movable to a second position for exposing the first and the second opening of the body, whereby a sensor strip can be pushed from the second opening of the body, the sensor strip thus being capable of being brought into sampling position when the shutter is in its second position.

One embodiment of a cassette according to the present invention comprises covers, a hub rotatably connected to the covers, a number of sensor elements arranged inside the covers, wherein the sensor elements are arranged one after the other as a spiral-like band, and the spiral is mechanically connected to the hub for transmitting force to the outermost sensor element of the spiral for pushing it out of the cassette when the hub is rotated.

One embodiment of a sensor element arrangement according to the present invention comprises a number of disposable sensor strips, each of which comprises at least one measurement area and electronic or optical contacts for analysing the sample arranged on the measurement area, wherein the sensor strips are arranged one after another in their longitudinal direction as a flexible band, from which the strips can be cut off one at a time.

Further, one embodiment of a method according to the present invention in which a portable health monitoring device is used, the device comprising a first means for carrying out the first step of the method and a second means for carrying out the second step of the method, wherein the health monitoring device comprises a shutter which in its first position covers the first and second means and the shutter is brought into the second position for exposing the first and second means and for bringing the first, second or both means into operation position, the first and second means are operated when the shutter is in its second position, and the shutter is returned to the first position.

Many advantages are achieved by means of the invention. It will accomplish an easy-to-use, easily transportable and compact device for repetitive measurement of blood indicators. The device can be brought into operation readiness or even measurement readiness with one movement (opening of the shutter). Subsequent to this, taking the blood sample is easy, because the exit opening of the lancet and the sensor are located under the same shutter and near to each other. Thus no separate parts, covers or devices are necessary. When the sample has been taken, the used sensor can be easily removed from the device with, for example, fingers or by rotating the device in hand so that the strip falls from its opening. Finally, the shutter can again be closed, whereby the device is again in its basic state.

While the shutter can act as an essential part of the cocking mechanism of the device, it will protect the device from dirt, dust, moisture and microbes of the environment, that, once on the needle or sensor, can be conveyed into the body or affect the measurement result, which can be very dangerous to the user. The operation reliability of the strips is typically also reduced during long-term exposure to ambient air and they are therefore usually stored in closed jars or individually packed. In a device according to the invention the openings of the lancet and the sensor strip are thus open to the environment only when the measurement is actually being carried out. Because all essential functions relating to taking the device into use and safety of use can be connected to the shutter mechanism, the device can be manufactured in the size of, for example, a sports watch (diameter about 5 cm) and it can be carried in pocket without a separate protective pouch. Even such a small device will nevertheless contain sensor strips for the usage of a day, typically for many days. The shutter can additionally keep the sensor strips chemically fresh. The small size of the device and the simple measurement operation encourage the diabetic to check the blood indicators often.

The device is small and it has a small number of moving parts, whereby its manufacture is inexpensive. Electronic or optical parts can be integrated thereto for, e.g. analysis, presentation of measurement data or data transfer. The device can be formed as a modular unit so that the lancet device of the lancet and/or the strips can be easily replaced. The device itself can be as a module comprising a functional unit, whereby it can be attached into a number of host devices.

Generally a blood sample measurement from a fingertip is very accurate, but the measurement devices are clumsy and the measurement operation is thus very difficult. Due to fast circulation, the blood sugar of the blood in the fingertips corresponds well to the general level. The shutter mechanism according to the invention can be used with one hand and even by moving just one finger. When the shutter is opened, the blood sample can be taken with one small movement from even one of the fingers of the hand holding the device. The shutter can further be closed with one hand. Thus the apparatus is also suitable for those with limited movability, such as one-handed persons, handicapped persons or paralysed persons with one hand inoperational or dysfunctional or for persons with inadequate control or stability of fine motorics between the two hands for carrying out a traditional measurement.

According to one embodiment the strips can easily be loaded into the device by means of separate strip cassettes. In this case the device comprises means for receiving the cassette and for transferring the force feeding the strips from the shutter or other interface means to the strip cassette or at least into one strip in the cassette. Correspondingly, the shape and mechanical design of the strip cassette and the strips must in this case be compatible with the device.

According to one embodiment the strips are loaded into the device as such, for example as a long band or one by one, whereby there's a space in the device into which the strips can be loaded as well as means for transferring feeding power from the shutter or other interface means into at least one strip located in the device.

In addition to measuring blood sugar the device can be used for measuring e.g. lactate transmitters in the blood. A person skilled in the art will also understand that in addition to analysing blood samples the device can be used for analysing other body fluids, such as tissue fluids.

By the second position of the shutter we here mean a position different from the basic state, the position making it possible to function in the operation zone for carrying out the measurement. The second position can further comprise several subpositions as will later be disclosed in more detail.

BRIEF DESCRIPTION OF THE DRAWINGS

In the following, the embodiments of the invention will be described in more detail with reference to the appended figures.

FIG. 2 is an explosion drawing of an exemplary configuration of a device according to FIGS. 1a and 1b.

FIGS. 7a-7d illustrate in side view a device according to another embodiment.

FIGS. 8a and 8b illustrate in perspective view a device according to yet another embodiment.

FIGS. 10a-10d illustrate a device according to a further embodiment.

FIGS. 12-12e illustrate an opening arrangement of a three-part device.

DETAILED DESCRIPTION OF THE INVENTION

In the embodiments illustrated hereinafter sensor strips (test strips) are typically used that are elongated and that have in one end a measurement area, into which a blood sample is arranged for analysing the sample. The measurement area can be on the surface of the device or in its inner parts and in other positions of the strip than its ends as well. There can also be a number of measurement areas in one strip, corresponding, for example, to different tests. The blood sample is arranged into the measurement area inside the strip by e.g. bringing it to one end of capillary arranged on the strip, wherefrom the sample is transferred to the measurement area capillarily. Typically, electrochemical analysis means are arranged near the measurement area. Thus, typically two electrical contacts (conducting areas) lead to the measurement area, through which the sample is analysed, typically resistively or capacitatively. The strip further typically has contact terminals which can accept an electrical connection from outside the strip. Alternatively, the analysis can be carried out photometrically, whereby the connection to the strip can also be optical. The strips are typically plastic- or polymer-based and their measurement areas can be protected. Suitable strips and strip cassettes are, for example the strips and cassette used the Accu-Check Compact Systems by Roche, Ascenzia Breeze strip and cassette by Bayer and the strip and cassette described hereinafter in this document.

Figure 1A:
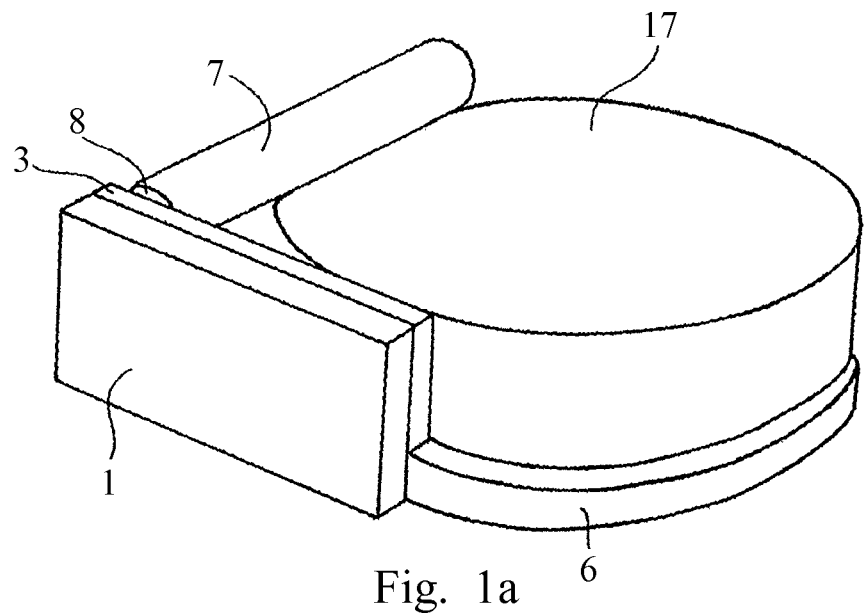
FIG. 1a illustrates as a perspective view a device according to one embodiment in its basic position.
Figure 1B:
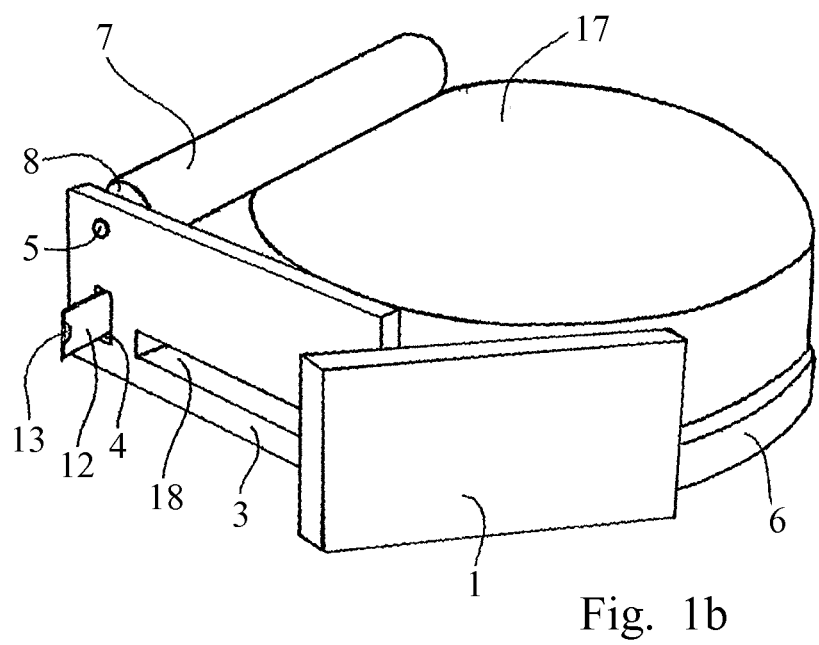
FIG. 1b illustrates as a perspective view the device of FIG. 1a in its operational position.

FIGS. 1-3 illustrate a preferred embodiment of a device according to the invention. FIGS. 1a and 1b show the device assembled in its basic and operation positions, correspondingly. The body is marked by reference number 6. In its basic position the shutter 1 rests over the operation zone 3 and in the operation position the shutter 1 is rotated away from the operation zone in relation to the body. The shutter can be rotated e.g. 30-90°, preferably about 45°. In the operation position the first opening 5 for the needle of the lancet and the second opening 4 for the sensor strip 12 arranged in the operation zone 3 are exposed. The shutter can be articulated into, for example, the centre part of the body so that the means connecting the body and the shutter runs along channel 18. The lancet device 7 is so arranged in relation to the operation zone that its one end 8 is aligned with the first opening 5. A space (housing) 17 is arranged into the device for sensor strips, into which the a number of sensor strips can be arranged. The sensor strips are arranged in the space 17 so that they can be brought one at a time partly in front of the operation zone 3 via the opening 4. The lancet device 7 can be attached to the body 6, operation zone 3 or the housing 17 or a number of these. The body, operation zone and housing can also be wholly or partially formed of one piece.

The distance between the first and second openings is typically 3-30 mm, preferably 5-15 mm. Thus taking the sample and conveying it to analysis can be carried out with small finger movements without moving the apparatus. There will, however, be enough space in the operation zone for carrying out the measurement. It will be obvious to one skilled in the art that the openings can also be consolidated into one opening. In order to avoid having impurities enter the device it will however be preferable to keep the opening/s as small as possible.

One preferable configuration of the device is shown in FIG. 2. The body 6 comprises a partly circular (elliptical) bottom part, onto the central part of which the fastening means 2 of the shutter can be pivoted. The fastening means can comprise, for example, a radial shaft, a curved guide and an extension into which the shutter can be fastened, as shown in the Figure. The fastening means 2 is arranged so as to be rotatable via the shutter along the level of the bottom part of the body 6 so that the extension of the fastening means travels along channel 18.

Sensor strips 12 can be arranged into the apparatus as e.g. a spiral band (belt) 15, into which they are arranged longitudinally. The strips can be cut one by one or they can be detached from the band 15. The strips can be fastened to each other or the band can comprise a narrow substrate strip into which the strips are individually fastened. The narrow strip can also have places for separate strips, whereby they can be added to the narrow strip, if necessary. The strip belt is mechanically, either directly or indirectly, fastened to the fastening means 2 for pushing the strips away from the opening 4, when the shutter 1 is slid or turned from the operation zone of the body along a continuous surface.

A solution in which the shutter 1 causes a new cut in the strip band already when closing the shutter 1, is mentioned as especially preferable. Thus, when the device is used again, the already cut strip is only brought forward for use. This is useful, as it is usually easier to use a large force (pushing) than when opening the device (pulling). Thus the cutting of the strip can be made to feel lighter.

The lancet device 7 typically comprises a spring 10 and a piercing head 9 which can at least partially be pushed through the opening 5. The lancet device is connected to fastening means 2 for conveying the force cocking the lancet to the spring 10. When cocked, the spring 10 has stored potential energy that can be released by means of a releaser. Upon release the piercing head is momentarily pushed out the opening 5 and then it again retreats inside the device in basic state. The releaser can comprise a separate mechanical means in the body 6, lancet device 7 or other part. The lancet device can be cocked either when opening or closing the shutter or by means of a separate cocking means.

The lancet means can also be electrically operated, for example in a way shown in EP publication 1 101 443.

The lancet means can also be integrated into the body or housing of the device. Thus, the tubular movement space of the piercing head is formed during the manufacture of the body or housing, e.g. during the casting or die pressing stage. Parts of the cocking mechanism of the lancet device can also be fixedly integrated into the body or housing.

Preferably the piercing head of the lancet means can be replaced. It can be, for example, arranged outside the device via a hole in the housing of the device, located opposite the piercing head of the lancet. Alternatively the whole lancet device can be rotated on the level of the movement of the shutter or in a level perpendicular to this direction, e.g. 45 to 90°, whereby the piercing head can be removed from the device. The lancet can also have a rotatable adjustment means, for example, for adjusting the hitting force.

The piercing head can also be replaced as in known lancet devices. In this case, a cap having an adjustment head is usually removed by, for example, pulling, whereby the lancet is exposed. The old lancet can now be removed and replaced by a new one.

The piercing head of the lancet device can also change automatically, whereby a new, unused needle is available for each piercing of the skin. It is obvious to one skilled ion the art that needles can be arranged inside the device in many ways so that they can be individually brought into operation position and subsequently removed or stored inside the device. A mechanical (or electromechanical) piercing head change system included into the device can also provided with a separate switch for using it. Thus the same piercing head can, if desired, be used many times, but changing the head is still very simple when compared with a fully manual change. Lancet magazines are disclosed in, for example, publications WO 2004110274, WO 03/071940 and U.S. Pat. No. 622,810.

According to one preferable embodiment the openings of the lancet and strips 5, 4 are arranged on top of each other perpendicularly against the rotation direction (level of movement) of the shutter 1. In an alternative embodiment the openings 5 and 4 are arranged essentially in the movement level of the shutter, whereby the device can be made thinner, but in this case the lancet device must be placed in the same level with the strip band. In both cases a very large proportion, even 50-75% of the inner volume of the device can be used for storing the strips. With the disclosed solutions it is possible to manufacture a device of the size of, e.g. a matchbox. Because the tip of the lancet is usually protected by the shutter 1, there is no need to pull its piercing head deep inside the device, but it can be left only 1 to 2 mm behind the level of the operation zone, for example. Thus the piercing means can also be kept small.

The shutter can be locked into operation position so that it can be returned to the basic position either by means of a separate shutter release or by applying a sufficient force on the shutter. Returning the shutter can be two-step procedure: in the first step the shutter is brought into an intermediate position, whereby the cutting means located in the device cut the strip ban so that the used strip can be removed from the device, and in the second step the shutter is brought into basic position for protecting the operation zone. A connection can be made to the strip either electrically or optically either directly after opening the shutter or as the strip is being pushed out or has been pushed out into the measurement position. Thus it is possible to ensure the strip is correctly placed and the calibration, detection and testing procedures of the strip can also be carried out. It is also possible to connect with the strip only at the first step of the returning step. The latter alternative can be advantageous in case it is desired to save operation energy. The analysis can be started automatically as soon as the blood sample has been brought into the measurement area. The device can also be provided with a separate switch for starting the analysis, whereby the analysis can be made at the desired time. On the other hand, this function can as well be included in the movement of the shutter.

Connecting with the strip can also take place at a different step of operating. These steps include, among others, cutting of the strip, opening of the shutter, closing of the shutter, cocking the needle device and releasing the needle device. The connecting with the strip can also take place in other parts (such as the contacts being first aligned, then activating the contacts), as an example in one of the above-mentioned steps.

The strip space and/or the lancet device of the device can be covered by means of, for example, a housing (shell) 17, the housing being openable or removable for replacing the strip band and/or the tip of the lancet or for servicing the device. The housing can be cup-like or it can consist of, for example, just a cover which can be arranged over a cavity formed by the body of the device. The shell can be designed so that when it is opened, it will expose, for example, the tip part of the lancet device, the rotation of which can adjust the strength of the lancet device. The tip part can also be removable for replacing the lancet. The adjustment tip and the cap of the lancet device can be adjustable as well and removable when the shell is closed.

As has been disclosed in the above, the shutter is functionally connected to the body of the device, it is especially functionally connected to the lancet device (or the actuator thereof) for cocking the lancet. It is also most suitably functionally connected to the strip feed device (i.e. "feed") so that the same hand movement that accomplishes the cocking of the lancet, can feed a separate strip from the strip feed device.

Preferably the device comprises a power transmission means functionally connected to the body and the shutter for transmitting the outwardly pushing power from the shutter to the strip being used. The construction of the power transmission means can comprise means obvious to one skilled in the art, such as gear wheels, rails, levers, threads, rolls, roll sets, springs and electrically driven means.

According to one preferable embodiment the space 17, into which the sensor strips can be stored, can be sealedly closed when the strip being brought out is in sampling position or otherwise away from the space 17 (such as being brought to the sampling position). If a band-like strip arrangement is used, the device will preferably comprise means for cutting the strip and for sealedly closing the space 17 when the strip to be brought out is removed from the band. Subsequent to this, before this or simultaneously with this the removed strip can be brought into sampling position. Cutting and closing the space 17 can be effected by means of the shutter 1 or some separate shutter or shutters. The isolation of stored sensor strips is important, because even a short-term exposure to oxygen, moisture or impurities can essentially deteriorate the measurement capabilities of the strip. Traditionally this has been prevented by storing the strips in a separate, sealedly closable vessel or individually protected. Individual protection will inevitably increase costs.

The strips can be brought into the device in a separate cassette as well. Thus, the device should include means for transmitting the power pushing the strips out via the cassette to the strips or directly to, for example, the uppermost strip of the cassette. According to a preferable embodiment the fastening means 2 has toothing aligned with the toothing on the cassette, whereby the strips in the cassette can be moved by the rotation of the shutter. The toothing can be designed to operate in one direction only, whereby bringing the shutter back to its first position does not suck the strip back to the cassette. The cassette preferably comprises an opening which can be aligned with the opening of the device 4. Various possible cassettes are disclosed later in this document. It is obvious to one skilled in the art how the different shutter mechanisms or other user interface means described in this document can be connected to various strip and cassette solutions by using existing mechanical and electrical constructions so that pushing the strip out and cocking the lancet device simultaneously or subsequently can be accomplished. Depending on the cassette or strip feed mechanism various toothed gears, rails, levers, threads, springs and electrically driven means can be used. Typically the device is mainly manufactured of a plastic material.

Figure 3A:
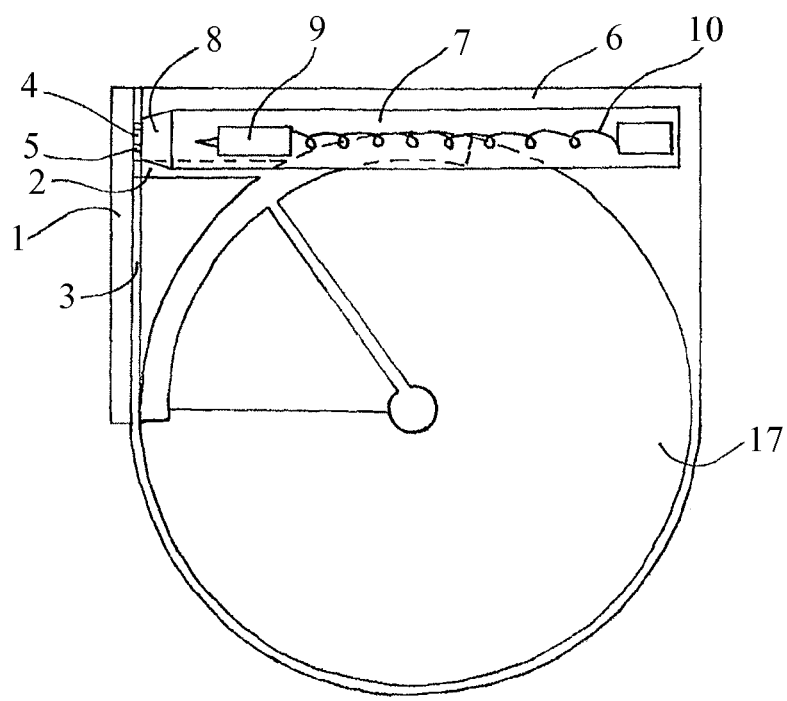
FIG. 3a is a cross-section of the device according to FIG. 1 in its basic position.
Figure 3B:
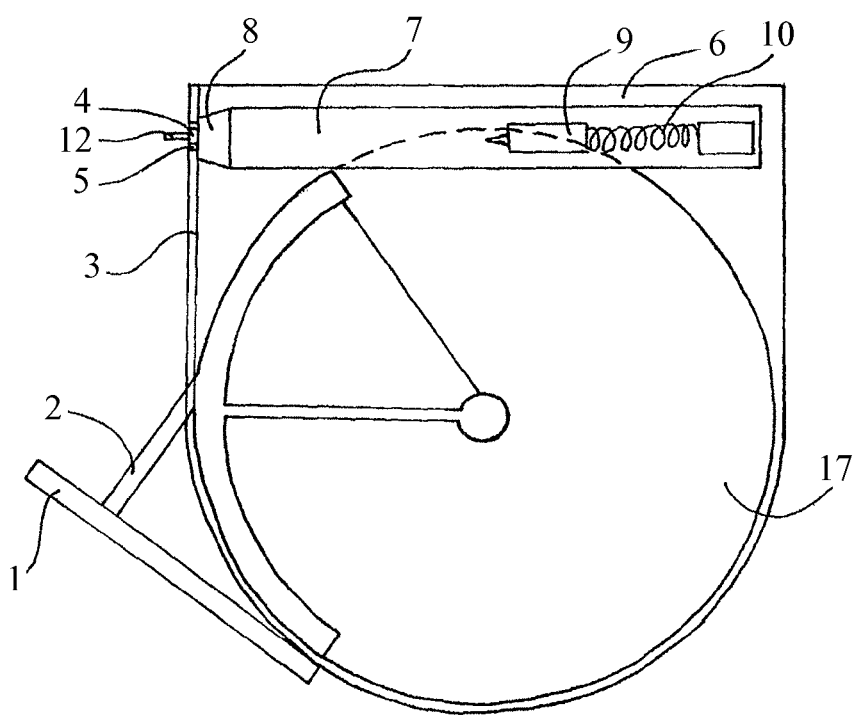
FIG. 3b is a cross-section of the device according to FIG. 1 in its operational position.

FIGS. 3a and 3b illustrate the above-mentioned embodiment in cross-section in its basic and stand-by states. The power transmission mechanisms are not shown.

Figure 3C:
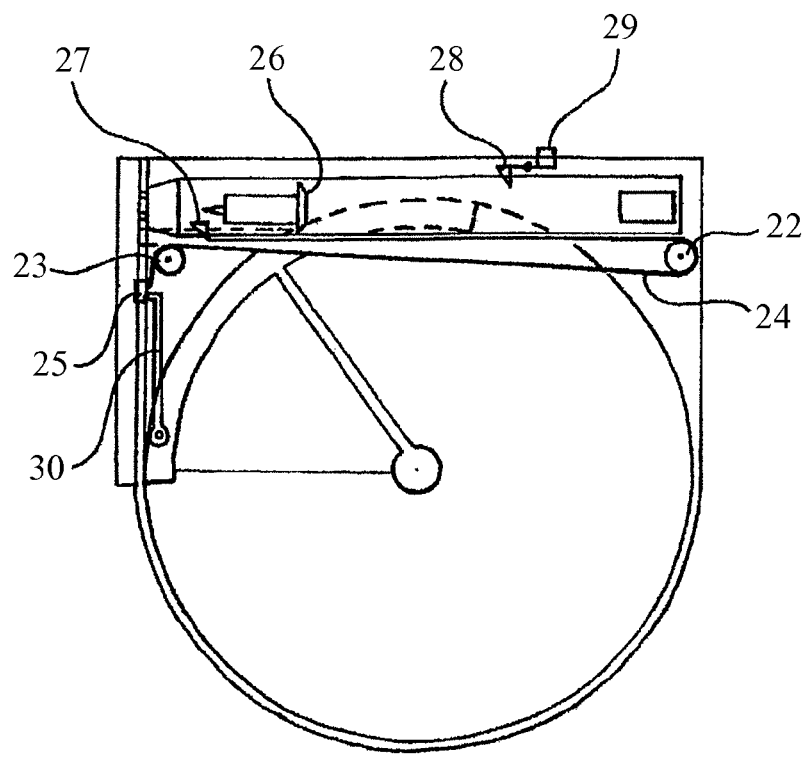
FIG. 3c is a cross-section of the operation mechanism of one embodiment of a device according to FIG. 1 in its basic position.
Figure 3D:
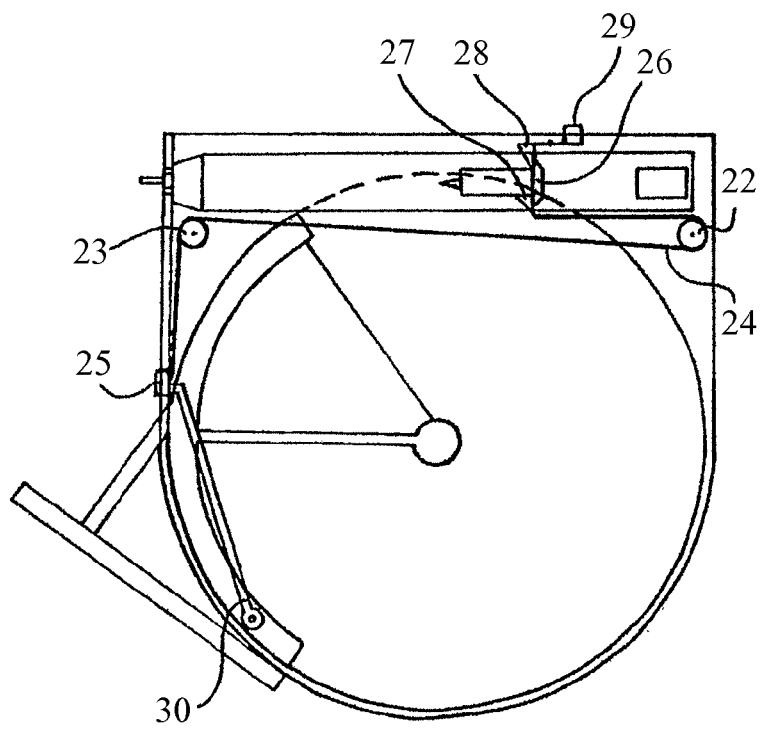
FIG. 3d is a cross-section of operation mechanism of the device according to FIG. 3c in the stand-by position of the device.

FIGS. 3c and 3d illustrate a possible method of accomplishing the cocking of the lancet device 7 with the shutter 1. In this solution two rolls 22, 23 are arranged inside the device, via which runs a thread or belt 24. The belt 24 is connected at its one end to the shutter 1 (sliding switch) and it runs through rolls 23 and 22 to the latch part 27. Connecting the belt 24 to the shutter 1 can be carried out by means of e.g. a sliding switch 25. The lancet is provided with a locking means 26 which is in its basic state a distance away from the latch part 27 so that the needle can be pushed out from the device when released. The latch part 27 will engage the locking means 26 upon turning the shutter and it will cock the spring 10 (not shown in this figure). When the spring is sufficiently cocked, the locking means 26 will be locked behind a bead 28, where by the lancet means is in its cocked state. Subsequent to this the spring can return the sliding switch and the latch part 27 to the basic state.

When the opening is opened, the cocking pin 30 can engage the sliding switch 25, whereby the cocking pin 30 catches the sliding switch automatically when the opening is opened. The pin 30 is arranged to be released from the sliding switch when the shutter is in its second position. The fastening of the pin 30 and the sliding switch 25 to each other can be accomplished by a known mechanical solution.

Subsequent to this the needle device can be released by pressing button 29 further connected to bead 28 for moving the bead. Thus the locking means 26 is released from behind the bead and the needle device moves at high velocity momentarily away from the device and returns to its basic state. The opening of the device remains opened.

If the blood sample is not sufficient, the needle device can be re-cocked with a sliding switch 25 preferably extending to the operation zone and be released many times, if necessary, without having an effect on the opening and the strip mechanism.

Returning the needle device to its rest state can be included in the closing of the shutter, if it has not been released. Upon closing the pin 30 returns into position from which it will again engage the sliding switch 25 when opened again.

Figure 4A:
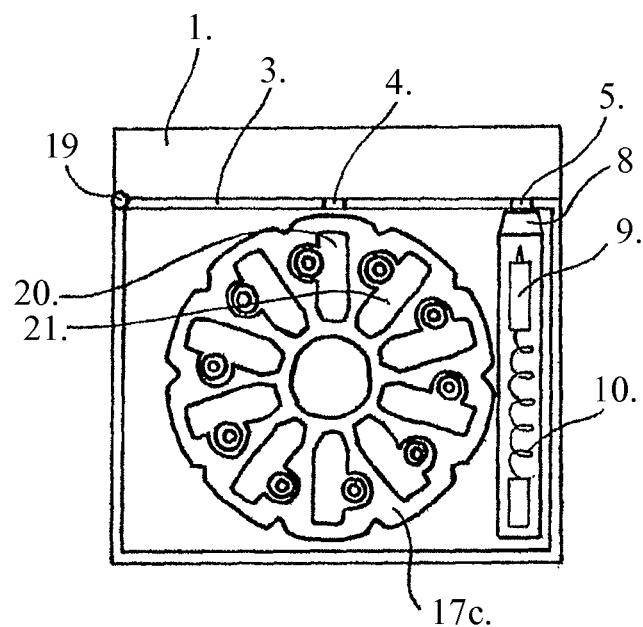
FIG. 4a is a cross-section of an other embodiment of the device in its basic position.
Figure 4B:
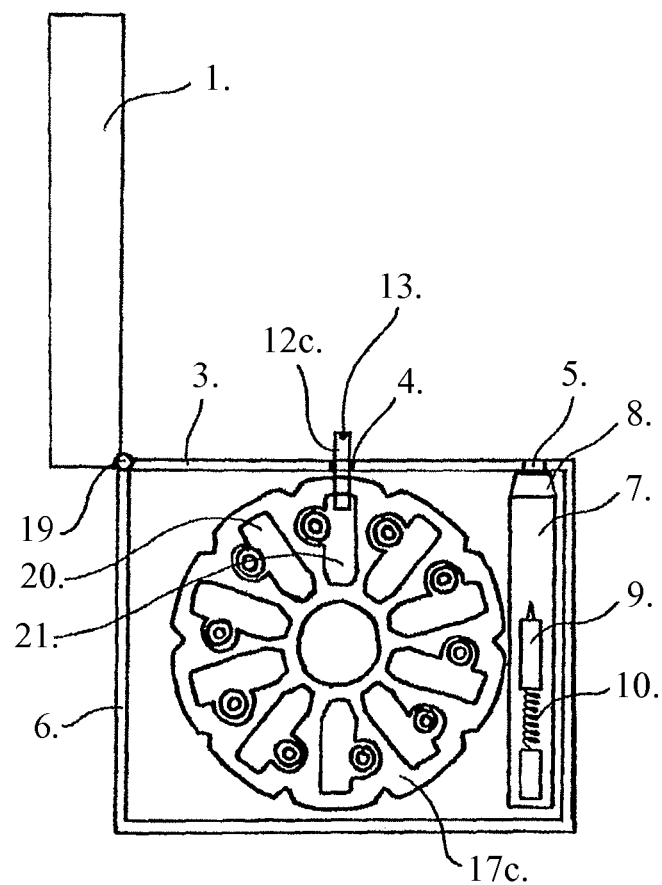
FIG. 4b is a cross-section of the device according to FIG. 4qa in its operational position.

FIGS. 4a and 4b illustrate an embodiment in which the shutter 1 is pivoted by its corner to the body of the device by means of a hinge 19. Thus the device resembles a traditional cigarette lighter and it essentially comprises the same parts as the first embodiment shown above. FIGS. 4a and 4b show an exemplary, different strip cassette solution in which the strips 12c are arranged radially on a rotating platform (cassette). The platform is rotatable so that the ends of the strips and the opening 4 of the device are aligned and the strip 12c can be pushed out the opening 4 with a movement of the shutter. The movement of the platform can also be connected to the shutter or the device can comprise dedicated means for rotating it. The power transmission can be accomplished via e.g. hinge 19 or a separate pin can be arranged between the shutter and the body for transmitting the force cocking the shutter and pushing the strip out.

Figure 5A:
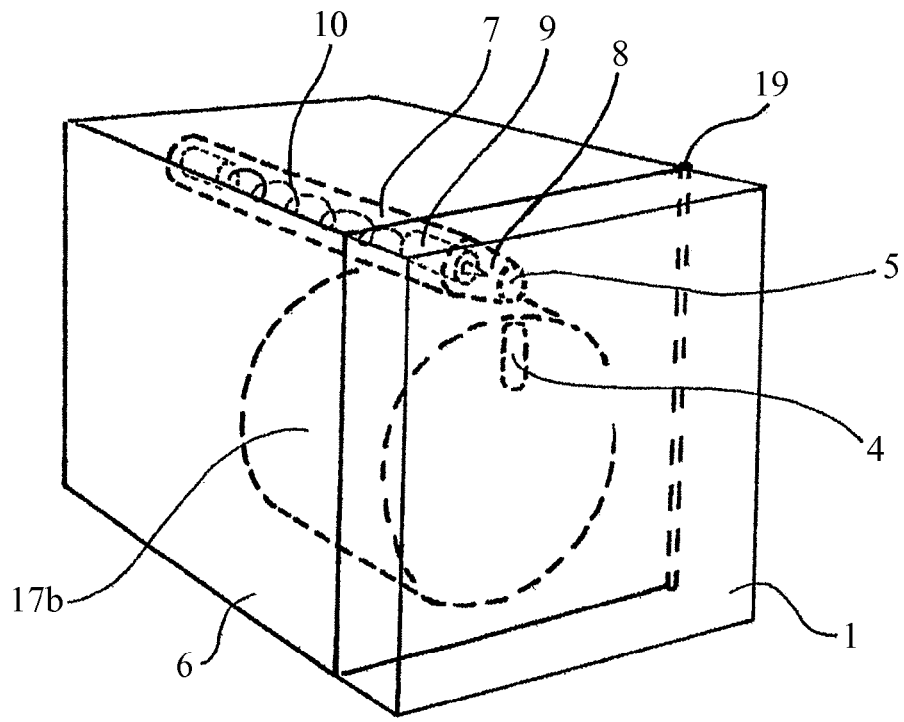
FIG. 5a is perspective view of the structure of a device using a drum-like strip cassette in situation where the shutter is in closed position.
Figure 5B:
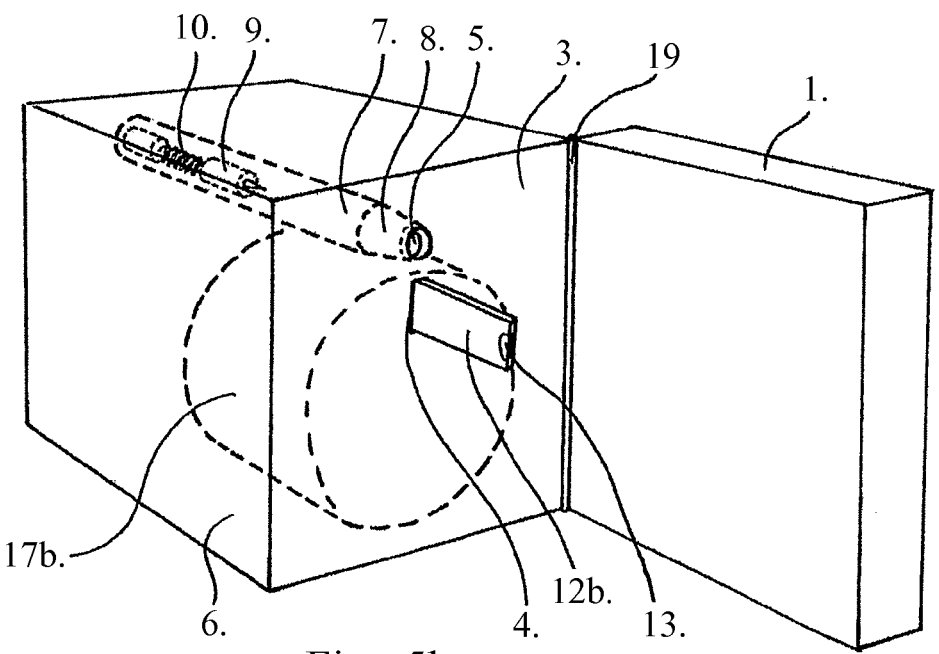
FIG. 5b is a corresponding view of a situation in which the shutter is in the open position.

FIGS. 5a and 5b show a device using a drum-like strip cassette 17b. In a drum-like cassette the strips 12b are arranged radially so that their second edges (the edges adjacent the end comprising the measurement area 13) are pointing towards the centre of the drum. The drum or the strip holder structure inside the drum is rotatable and the strips can be pushed out of the drum one at a time through the shutter 1.

Especially in the case of the embodiments shown in FIGS. 4 and 5 the shutter can be realised also so that it moves in the level of the operation zone 3 by means of a pivot arranged in another direction. The way of realisation depends, among others, the feed mechanism of strips or the shape and operation of the strip cassette.

Alternative embodiments of the invention are further shown in FIGS. 7-10. FIGS. 7a to 7d show a construction in which a first shutter part 71 and a second shutter part 77 slide in relation to each other unidirectionally linearly. In their basic positions the shutter parts 71 and 77 form a closed enclosure. When the enclosure is opened, the body of the device and the operation zone 73 are exposed from under the shutter. Both shutter parts can be attached separately and in a slidable way to the body, whereby a multi-part opening movement can easily be accomplished, as is described in more detail in connection with FIG. 12.

The seam 79 is preferably bevelled in relation to the movement of the direction at least at two sides. The length of such a seam increases in relation to length of a seam perpendicular to the direction of the movement, it has been noticed that with a bevelled seam the sealing is much better than with a seam parallel to the direction of the movement. This is because when the parts are pressed together, the bevelled surfaces also form a force component perpendicular to the direction of the movement between the parts. In addition an enclosure according to FIG. 7 can easily be opened with one hand.

FIG. 8 shows a rotatably openable and closable device in closed (FIG. 8a) and open (FIG. 8b) states. Thus the operation zone 83 is exposed when the shutter 81 is rotated in relation to the cylindrical body 87. Typically the operation zone is located between the shutter and the part of the body visible when closed, but it can also extend from the end of the device, like a bar of balm from a lip balm tube.

Figure 9A:
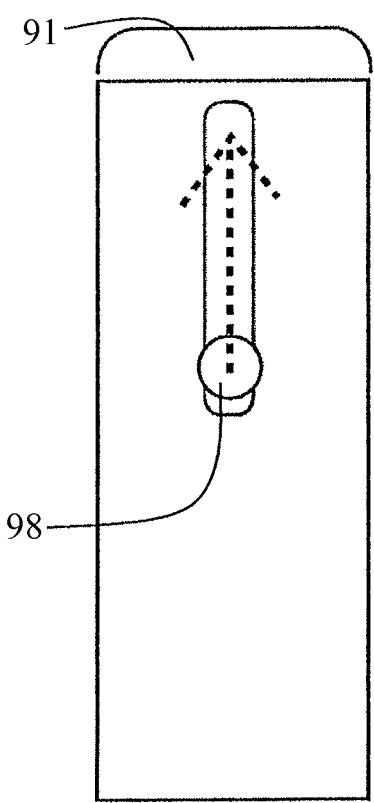
FIGS. 9a and 9b illustrate in side view a device according to another embodiment.
Figure 9B:
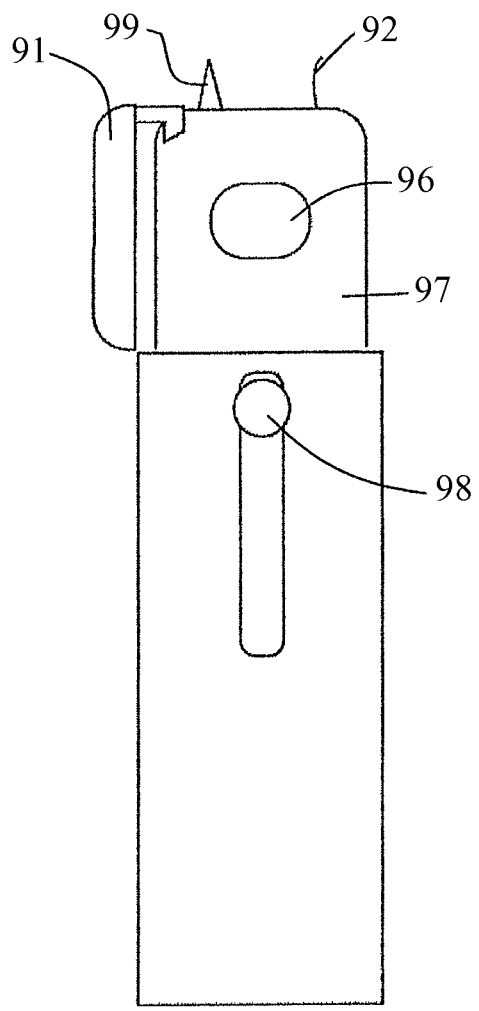

FIG. 9 shows a device solution working with the principle of a stiletto/push out. In the basic position the shutter 91 totally covers the body. In the operation position the body is at least partially pushed out from under the shutter, simultaneously bringing exposing the operation zone. The exposed needle of the lancet is marked by reference number 99 and the sensor strip is marked by reference number 92. The body 97 can be moved in relation to the shutter 91 by means of e.g. actuation means 98, whereby the body opens the cover of the shutter upon being pushed out. When brought out to the operation position the lancet release 96 is also preferably exposed. As can be seen from the figure, the shutter can comprise two parts and be articulated so that its second part is in basic position over the operation zone and tightly against the second part and/or the body. The cover of the shutter 91 can also comprise two parts and it can be realised as a sliding one instead of being articulated. The shutter and the actuator means can also be combined.

FIG. 10 shows yet another embodiment. The shutter is marked with reference number 101, the strip with reference number 102 and the lancet with reference number 109. The body is arranged to slide in the basic position essentially totally inside the shutter 101. FIG. 10b further shows the strip loading opening 117. FIG. 10c shows an exemplary opening mechanism. In the operation position (middle picture) the strip and lancet openings are visible and when the device is further opened, the strip loading opening is exposed as well.

FIG. 10d shows a key fitting into the indentation or other zone 115 shown in FIGS. 10a and 10b. The shutter of the device can not be opened without the key or the device, especially the lancet, can not be otherwise used. Such a locking mechanism allows an easy access prevention of other persons, such as children, into the delicate and/or hygienic parts of the device. The same idea can naturally be applied to other embodiments of the invention as well.

A device according to FIG. 10 can also be accomplished without a key, whereby there can be, in the vicinity of zone 115 (as well as for example along the edges of the "cover") a place or places formed so that the body can be pulled out from the shutter 101 with fingers.

Figures 11A, 11B, 11C, 11D:
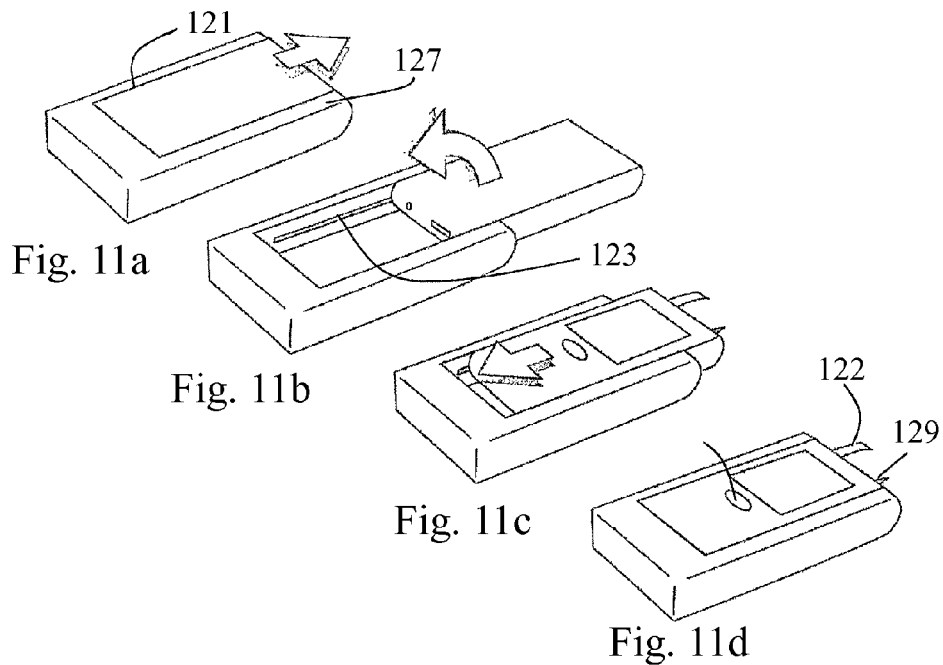
FIGS. 11a-11d illustrate a device according to yet another embodiment and its use.

FIGS. 11a-11d show as a series a device according to one preferable embodiment and the way of preparing it for use. The shutter is referred to with reference number 121 and the body part of the device with reference number 127. In the first step (FIG. 11b) the shutter 121 and the body 127 are pulled along rails therebetween, typically linearly, into a position in which rotation between the shutter 121 and the body 127 is possible. They are subsequently rotated in relation to each other typically 180° so that they are again in essentially the same level (FIG. 11c). The shutter and the body can further be locked into operation position by sliding them again along the rails (FIG. 11d). The cocking of lancet and feeding of the strip, cutting and other functions related thereto can be carried out in any of the above-mentioned steps or when closing the device again.

Figures 12A, 12B, 12C, 12D, 12E:
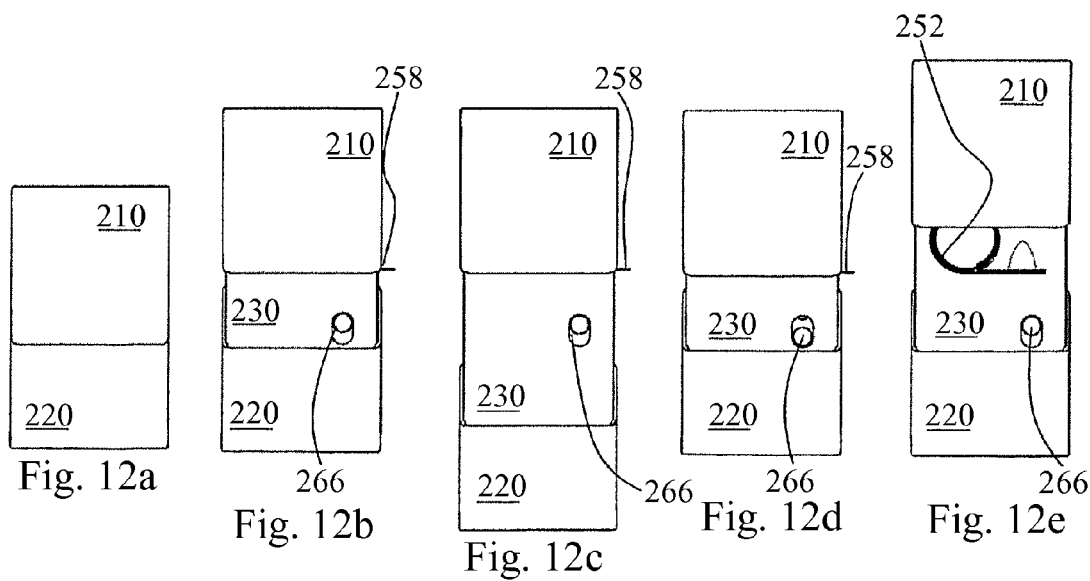
Figure 13A:
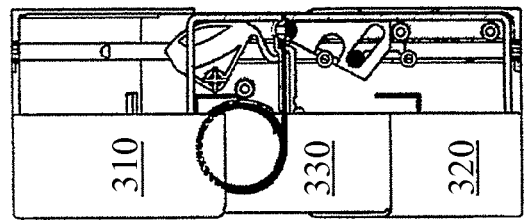
FIGS. 13a-13e illustrate in more detail the strip feed and cutting mechanism of a three-part device.
Figure 13B:
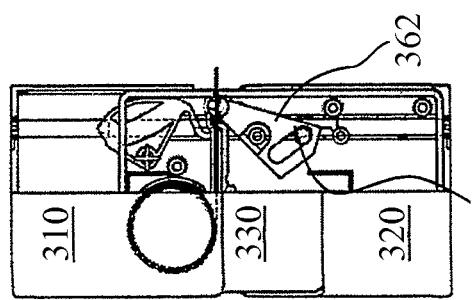
Figure 13C:
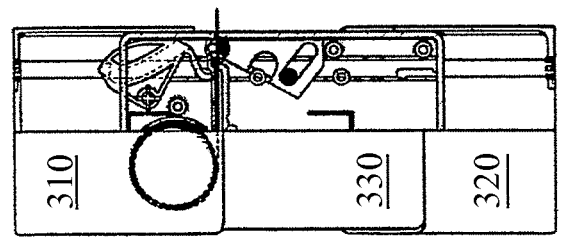
Figure 13D:
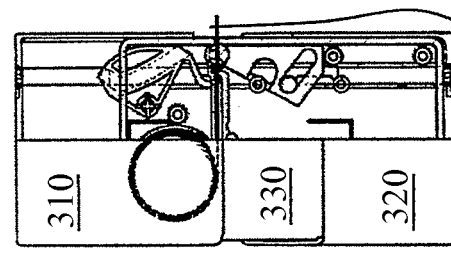
Figure 13E:
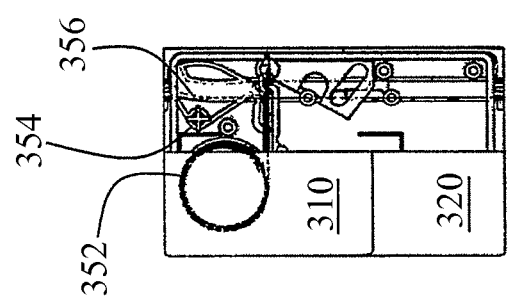
Figure 14D:
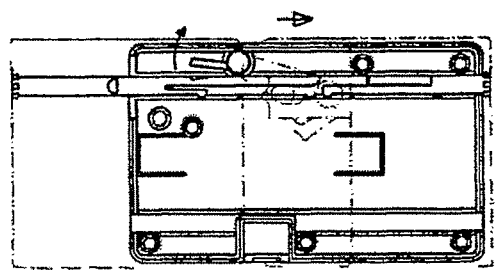
FIGS. 14a-14d illustrate a mechanism for phasing the opening of a three-part device.
Figure 14C:
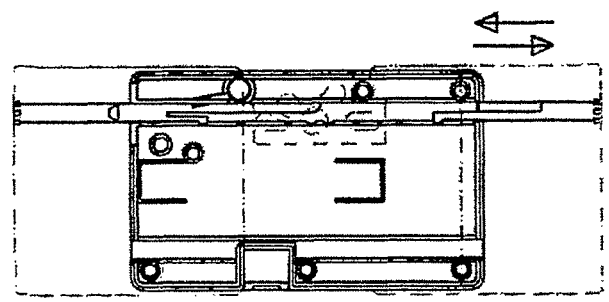
Figure 14B:
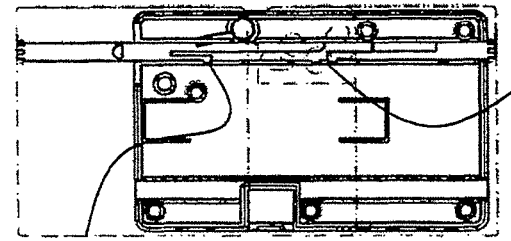
Figure 14A:
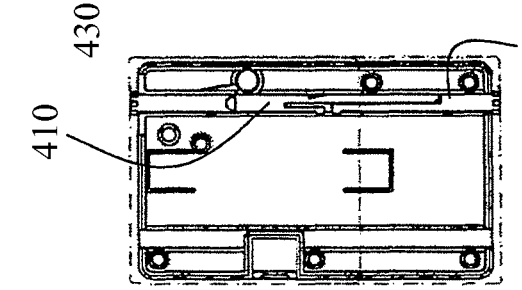

FIG. 12 shows in more detail an exemplary opening arrangement of the device of FIG. 7 comprising a two-part shutter and a bevelled butt seam. The first and second shutter part 210 an 220 slide independently in relation to the body 230. The operation of the device is begun (FIG. 12b) with a movement of the first shutter part 210, whereby the body 230 with its operation zone is exposed and a new strip 258 is pushed out from the side of the device. The lancet can be cocked with a movement of the second shutter part (FIG. 12c) and further be released with a shutter or a separate release. The strip band cutting switch is marked by reference number 266. When the first shutter part 210 is further moved in relation to the body 230 (FIG. 12e), the strip band 252 is exposed and can be replaced in this position. Typically the lancet is pushed out from the other side of the body of the flat device.

FIG. 13 shows in more detail an exemplary mechanism for accomplishing the above-mentioned functions. When the first shutter part 310 is pulled, the feed means 356 pushes one strip 358 out from the side of the device, whereby the rolled strip band 352 rotates a corresponding distance. Here, the feed means is pivoted to the body 330 of the device with the pivot 354. Cutting of the strip band by the switch 366 is effected by a cutter 362 functionally connected thereto. Here, the cutter is rotatably connected in relation to the body 330. The cutting head 362 of the cutter moves during cutting close to the fixed opposing part of the body, which together cut the strip band 352 a bit like scissors.

The operation of the needle device is not illustrated in FIGS. 12 and 13, but it can be carried out as previously described. We have found that in connection with this embodiment it is especially preferable to have a solution in which the needle can be extended out. The movement of the shutter (preferably that of the first shutter part) pushes the lancet device in the plane of the figure, whereby its tip part is better exposed for the measurement. Subsequent to this the cocking of the lancet device can preferably be continued with the second shutter part. After the measurement, when closing the device, the needle device retreats back inside, still accomplished by the shutter mechanism. This solution can correspondingly be carried out with any of the above-mentioned embodiment of the device. In addition to the lancet means, when the shutter is opened and closed, other parts (especially the needle device and the strip opening/belt) can move for accomplishing a better measurement position. The parts of the device can move also when other user interface means are used, for example when using a separate strip feed lever.

FIG. 14 shows a mechanism by means of which a phased movement of the shutter parts can be accomplished. The first and second shutter parts are connected to bars 410 and 420, correspondingly, the bars comprising suspended extensions 430 and 440 or corresponding means for locking their position in relation to the body (FIG. 14a). When the bars are overlapped in their first position, the extension 440 can not move away from its groove, whereby the second shutter part can not slide in relation to the body. The first shutter part can instead be slid into operation position (FIG. 14b), whereby the movement releases the extension as well and thus makes the movement of the second shutter part possible (FIG. 14c). The housing can be closed in opposite order (FIG. 14d). It is not necessary to lock the second shutter part down, because it is only used for cocking the needle device. The first shutter part can be locked down by means of a bead/groove mechanism 430. The locking into the open position can be released in connection with e.g. cutting of the strip or when a suitable force is applied on the shutter part.

The device can also be manufactured to be directly worn on a person. Thus the device can comprise a housing formed as, for example, a wrist band or a piece of jewelry, the housing containing the essential parts of the device. The shutter can, for example, slide along the circumference of a ring. When the shutter is pulled into another position, the ring is "cut", i.e. its two ends are visible. The lancet device can be arranged into one end of the ring and the strip feed can be arranged in the other end.

In all models a seal can be arranged between the shutter of the device and the body or between the shutter parts or the interface surface between them can in the basic position be made sealed by means of another solution. The operation zone and the inner parts of the device are thus protected from dust, dirt and moisture and the device can be transported in, e.g. pocket.

Figure 15A:
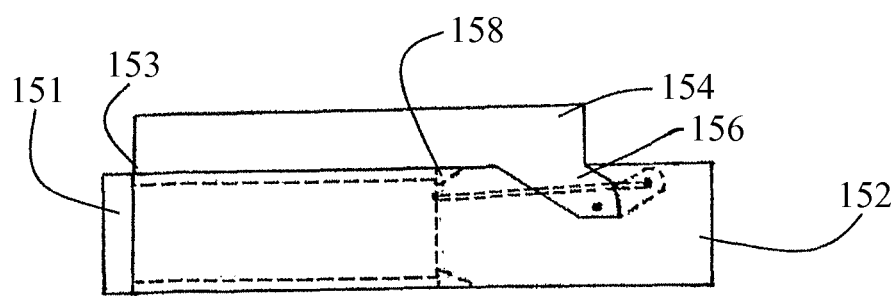
FIGS. 15a and 15b illustrate in cross-section a further embodiment of the device.
Figure 15B:
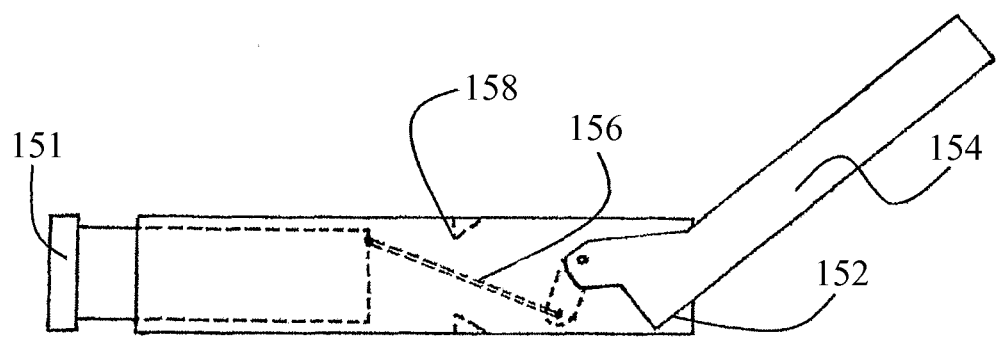

FIGS. 15a and 15b further show an embodiment comprising a shutter 154 functionally connected to the first 151 and the second 152 housing part, the shutter being arranged to move between at least two different positions (Figures a and b, correspondingly) so that in one position the first 151 and the second 152 housing part are locked against each other so as to form a tight seam 153. This can be accomplished for example so that the shutter 154 is rotatably pivoted to the second housing part 152 and the device comprises means 156 for changing the rotation movement of the shutter 154 into the sliding movement of the first housing part 151 in relation to the second housing part 152 for exposing the operation zone. The means 152 can comprise, for example, a rigid or elastic elongated means being pivoted by its one end to the shutter 154 and by its other end to the housing part 151. The rotation movement and the means 152 are arranged so that when the shutter 154 is in the closed position (the first position of the device) the first housing part 151 and the second housing part 152 are constantly being pressed against each other and the shutter 154 is pressed against the second housing part 152. The figure also shows extension 158 which can be arranged on the inner surface of the second housing part 152 so that another tight seam is formed between the rear edge of the housing part 151 and the second housing part 152.

Especially in this embodiment it is preferable to use a seal, most preferably a somewhat elastic seal at the seam 153. When closing the shutter 154, when the first and second housing parts 151, 152 meet at the seam area 153, the spring force of the seal causes a force against the closing. At some point (usually when means 156 connecting the shutter 154 and the first housing part moves over the pivot of the shutter 154), the direction of the force is changed. Thus the spring force of the seal keeps the shutter 154 closed and the seam 153 sealed.

A corresponding mechanism can be fitted to the outside of the device as well, connecting to the visible outer surface of the first housing part 161. Thus no extra components are needed for a sealed inner area. As a person skilled in the art will understand, such a geometric spring-assisted locking of the shutter and sealing of the device can also be attached to any other embodiment.

The shutter 154 can also comprise one user interface element, for example a display and/or buttons.

The spring-assisted mechanism can also be arranged inside the device, as has been shown in publication JP 2004/253526. In this case the operation of the spring mechanism is caused by moving the shutter or shutters of the device and no separate actuation means is necessary. Such a method can as well be attached to any embodiment of the device, including embodiments utilising rotatable or pivoted movement. The spring mechanism can be positioned so that it presses the seam together when the seam is closed, thus improving the sealing of the device.

According to one embodiment the device includes means for cocking the lancet device independently of other functions. This is advantageous if the first release of the lancet does not hit the skin so that the necessary blood sample can be collected. Such a cocking bar can be arranged e.g. directly on the lancet means 7 or under the shutter 1 at the operation zone 3. The cocking of the lancet means can also be carried out so that the shutter is arranged to open in many steps. The strip is pushed out in the first step and when the movement is continued, the lancet device is cocked. The shutter can be arranged so as to lock after the first step, whereby the lancet device can handily be cocked again with the same rotating, turning, or sliding movement as in normal use. In a typical use, when the lancet device is released, the piercing head is quickly expelled through the opening 4 and then returns to the basic state, whereby the piercing head is totally inside the device. The device can also comprise a lancet device decocking mechanism allowing the release of the piercing head without expelling the piercing head.

According to one embodiment the feeding of the test strip and/or the lancet device is carried out electrically when the shutter is opened. In this case the device preferably includes a sensor arranged to detect the opening of the shutter and to transmit an electric signal to the feed means of the test strip and/or the cocking means of the lancet means. The lancet device can be cocked e.g. magnetically. According to one embodiment the lancet is wholly magnetically operated, whereby no spring is necessary for moving it. Thus, the cocking of the lancet means bringing the electrical, magnetic or mechanical mechanisms into operation readiness so that it is possible to use the lancet in the piercing step. Thus the piercing force is transmitted to the piercing head of the lancet directly, for example with coils using the operation principle of a relay.

The device can comprise a small stepper motor for feeding the test strips, the motor rotating the strip band directly, transmitting the movement to the strip cassette or carrying out the pushing of the strips one by one out of the strip opening, according to the strip system. The above-mentioned functions relating to both the strips and the needle device can also be activated from one or more separate switch/activator.

Contact means are preferably arranged near the feed opening of the strip, inside the device or at the edge thereof, the contact means being connectable to the conductive areas of the strip in measurement position for carrying out the blood analysis. The contact means can comprise, for example, spring-loaded conductive surfaces that are pressed against the conductive areas of the strip as a consequence of the movement of the shutter and or releasing the shutter for forming an electrical contact with the strip. The contact means can also comprise strip-like brushes sliding against the strip belt so that they form a contact with the first (in measurement position or coming there) strip of the strip belt. The contact means are connected to the analysis electronics of the device and/or data transfer devices for connecting a trigger potential or an optical signal to the sensor and for transferring the measurement data forward to the electronics of the device.

The device can comprise an analysis circuit based on electronic components or data processing elements, the circuit computing into the memory of the device or a host device, such as wrist computer, computer, mobile phone or the like, e.g. the blood glucose from the signal transmitted from the strip. The analysis electronics can be installed e.g. into the inner surface of the device or it can be embedded into the body material. The same device or different versions of the device made for different purposes can also comprise means for getting other measurement results from the same or different samples, as is obvious to one skilled in the art.

The device can comprise a display. The display can be installed directly into the body or, for example, into a shell (housing) installed over the body. The display can show, for example, time of the day, the recommended time of the next measurement, the estimated current blood sugar value, descriptors, curves or user interface elements. The user interface allows, for example, scrolling to previous measurement values and setting reminders for the next measurements.

The area exposed from under the cover or other areas of the device can comprise a display, various lights, a speaker for sound reproduction, microphone, keys, other touch-sensitive or otherwise sensitive elements capable of transmitting information with all known methods from the user to the device (buttons, other moving or pressure-sensitive parts, sound) and vice versa (lights, colours, sounds and so on).

According to one embodiment there is a backlight in the display, the light being preferably arranged to turn on when the shutter is opened and to turn off when the shutter is closed (or after a predetermined time from this). According to one embodiment a source of light is arranged on the operation zone or in its vicinity, beside the shutter or under it. The source of light can comprise e.g. a bright-light LED that will light the area before the operation zone like a flashlight when the shutter is open. Because of the display and/or operation light measurement and reading the results can also be carried out in poorly lit areas.

Other possible functions of the device are, for example, calorie counter, GPS tracking, wireless connections to other devices, clock, calendar, data storage and transfer, processing of measurement data, calculating averages and extreme values, showing descriptors, various tables with their data processing possibilities, pulse meter and service sets derived from these for health care or the like. The device can also comprise auxiliary devices for emergencies, such as a fructose capsule or pastille, guidance for others in case of emergencies, an injection releasing the sugar reserves in the liver (e.g. Glukagon). The device can also include accessories needed for the measurements, such as cleaning wipes (for cleaning the sampling place of the skin). The device or its part (strip storage) can also include elements improving the durability of the strips, such as a dehumidifier, which can preferably be replaceable, most preferably always replaced when a new strip cassette or cassette-less strip system is loaded into the device. The parts of the device subject to wear, such as seals, can be replaceable.

Data transfer with a host machine can be implemented in the device so that the measured values are automatically or periodically transmitted to a mobile phone kept, for example, in the pocket, to a health care data base, the relatives of the patients (parents or family). An alarm to another device or other devices (wirelessly to the mobile phone of a parent) can also be arranged for emergencies. For child patients, the notification of the blood sugar level can be made automatically to, for example, the mobile phone of the parent always after the measurement.

The device can comprise wired or wireless data transfer components for transferring raw measurement data or calculated blood sugar values to a host device, such as a computer or a mobile phone. The data transfer can also be carried out via a USB or Bluetooth bus. The device can also comprise memory capacity for storing the measurement data or determined blood sugar values.

The device can comprise a battery or a rechargeable battery as an energy source for electrical functions.

According to one embodiment data about the nutritional values of various foodstuffs or food portions can be entered into the device in advance. Thus, it would be possible to enter data about nutritional input during meals. The device can use the data e.g. for predicting the current blood sugar value. Such a system is disclosed in WO publication 01/13786. The device can also comprise learning mechanisms, whereby it will adapt to the body and nutritional habits of the user and will, for example automatically alarm or remind. The device can be continuously in functional connection with other devices, such as a step or pulse meter providing data about load and sugar consumption.

The device can comprise a hole or a loop for fastening to a key fob or the like, a belt clip for carrying the device on the waist or some other known fastening or transport mechanism. It can also be integrated into e.g. a wrist watch or a wrist computer either as an independent unit or combined with the electronic parts of the host device. This allows using the calculation or visualisation capacity and the user interface of the host device. The device can also be integrated into e.g. a PDA or a mobile phone or to the removable shell of such. The device can use the battery or other energy source of the host device.

The device can also be planned for integration into smart apparel. The above-mentioned functions of the host device can also be used if the device is connected or can be connected to a host device with a wireless uni- or bidirectional data transfer link.

As has been stated in the above, the device can be designed also so that the shutter will in the first position protect the first and second opening and can be brought into the second position without immediately cocking the piercing means and/or pushing the sensor strip. Thus the opening of the shutter will only allow use of a separate cocking device or devices for accomplishing the above-mentioned operations.

The above-mentioned embodiments can be modified to suit very different strips or strip cassettes. The test strips can be located in a strip cassette loosely e.g. in a stack or fastened to each other by their edges. The cassette can be, for example, rectangular, disc-like or cylindrical. Various known test strip cassettes are described in U.S. Pat. Nos. 5,575,403, 5,489, 414, 4,218,412 and WO publication 03/082092. For example, in case of the disc-like cassettes shown in U.S. Pat. Nos. 5,575,403 and 5,489,414 the force moving the strip can be transferred from the shutter to the strip by means of a rail arranged in the device, the rail transforming the rotation movement of the shutter into a linear movement.

Below is a description of a novel kind of a strip cassette which is especially well suitable for use with small measurement devices having a multi-function shutter mechanism.

Figure 6A:
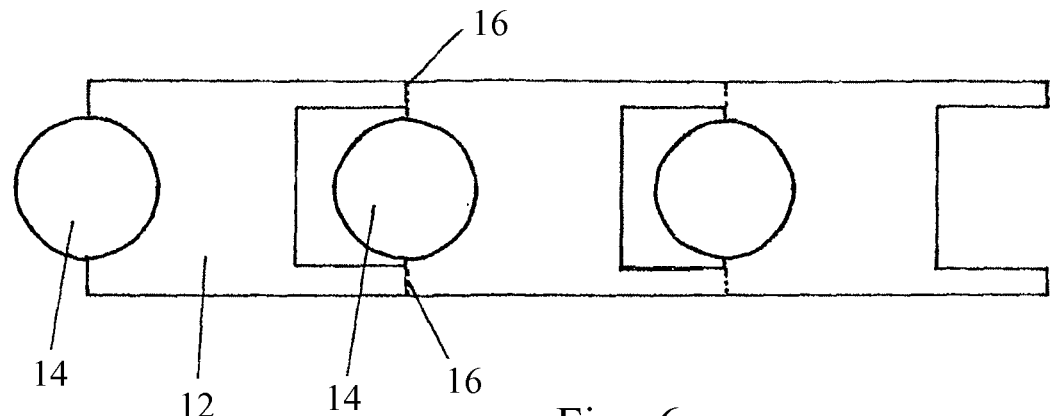
FIG. 6a is a top view of an embodiment of a strip belt used in the invention.
Figure 6B:
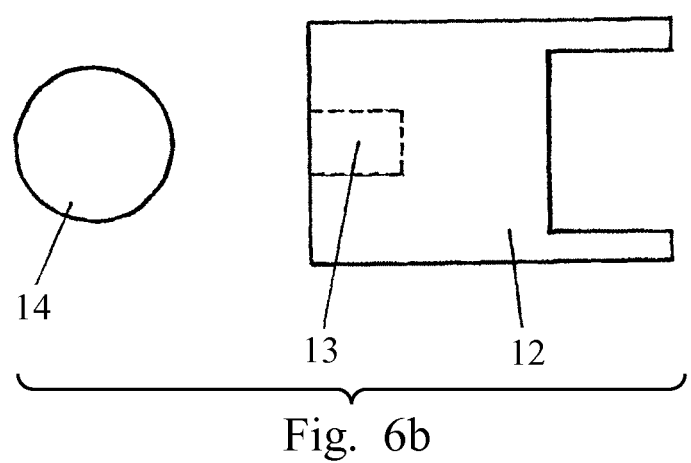
FIG. 6b is a corresponding top view of the parts of individual sensors.

A test strip set can contain test strips arranged in a continuous spiral-like belt. The strip cassette is placed inside the measurement device so that its opening (exit zone) aligns with an opening protected by a cover in the body. The strip cassette can be closed or open. A closed cassette can function simultaneously as a housing for a measurement device. As can be seen from FIGS. 6a and 6b the cassette comprises a number of disposable elongated sensor strips 12 arranged in a housing one after the other in their longitudinal direction as a flexible strip, each sensor strip having a sampling area (measurement area) 13 and contacts connected to the sampling area for analysing the blood arranged to the sampling area. The cassette further comprises a hub rotatable in relation to the shell of the cassette. The first strip of the strip band is arranged into the hub so that when the hub is rotated the strip belt is moved towards the strip exit zone of the cassette. Preferably, the hub is provided with a toothed part or a part having an inner friction surface, into which it is possible to mechanically connect from the outside of the cassette for rotating the hub. A cassette having one hub is especially well suitable for use with a health monitoring device having a multi-function shutter as described in this document.

The sampling areas 13 of the strips can be protected by protective stickers 14 that can be removed prior to bringing blood on the strip. In addition to stickers it is possible to use plastic foils or other foils and plastic pieces formed for the purpose. Please note that a larger part of the strip than the sampling area, even the whole strip, can be covered. Removal of the protective sticker can be done either manually or automatically before the measurement. A cutting zone 16 can be located between the strips for separating the strips from each other manually or automatically using the cutting means of the device. Typically the cutting zone is located between the edge of a sensor element having the measurement area and the opposite edge of the next sensor element. The cutting means can comprise e.g. at least one cutter or blade that moves to the cutting zone when the shutter is moved and cuts the strip band. The cutting can alternatively be done, for example, by bending the strip band so that the band is cut at the area of the cutting zone. The cutting function can be connected to the opening or closing step of the shutter or to both of these in two steps. The cutting function can alternatively be produced by means of a separate actuation means. The same movement or a different movement can be used for releasing the mechanism holding the strip, if any. The strip can also further be removed from the device by, for example, dropping when the device is kept in a suitable position.

The cutting of the strip belt can also be connected to the release of the lancet device or to a separate function.

The contact areas in the strips can continue over the whole strip belt, whereby the sampling area of a strip at the first end of a strip can be monitored from the second end of the strip or from another location of the strip. Typically connection is, however, made separately to each strip by means of contact surfaces located near the exit opening, the surfaces engaging the conducting areas of the strip when the shutter is moved, for example.

Generally, the strip band does in fact comprise a number of disposable sensor strips, each of which comprises a measurement area and contacts connected to the measurement area for analysing the blood arranged on the measurement area. The sensor strips are arranged as a flexible band in their longitudinal direction. Such a band can be rolled into a spiral and pushed out of the health monitoring device one strip at a time. The band can comprises grip areas, such as indentations at the sides of the strips for helping the pushing out of the strips. According to a preferred embodiment the measurement areas are protected by removable protective stickers. Further, the sensor elements are preferably attached to each other so that a cutting zone is formed between them, where the band can easily be cut for removing the used sensor strip from the band.

A device according to the present invention can be accomplished by means deviating from the above description. Thus, the device can comprise a switch releasing the strip from the measurement connections/holders for preventing accidental dropping from the opening.

The needle device and/or the strips can also be included in the opening protective cover.

The cover can also be totally removable from the device, i.e. the device can in a way consist of two modules, the separation of which means in this context the same as opening the cover (the movement cocks the lancet). The removal can also include rotation, sliding or some other corresponding movement.

Sensor strips containing a lancet or a corresponding piercing head integrated with the strip for piercing the skin can also be used in connection with the above-described device and sensor strip arrangements. Such sensor strips are described in e.g. publications WO 2004/066822, US 2006/079810 and WO 2006/001973. Such strips can as well be arranged as a band, stack or some other configuration. Especially in devices of this kind the first and second openings of the device are arranged as one opening, from which both the lancet and the sampling area of the strip can be brought out. In such a device the lancet is usually arranged to be movable in relation to the strip and the device comprises means for transferring actuating force to the lancet combined with the strip. Thus the lancet can pierce the skin with a stabbing movement like of a normal lancet device. The strip and the lancet can also move together for accomplishing this. However, if the lancet does not move, the piercing of the skin can be accomplished e.g. manually by pressing the skin against the lancet/strip.

On a very general level the basic idea of the invention is applicable, in addition to measuring the blood and tissue indicators, to other personal medical, chemical or physical and the like health monitoring measurements made externally of the body in two or more steps. The method can be accomplished by using a device as described above, in which the operation zone comprises means for carrying out the first (piercing) and the second (analysis) step of the measurement. Thus it comprises a method step in which the shutter is moved for exposing the operation zone and for preparing the measurement devices for use and a method step in which the second measurement step is carried out adjacent the operation zone. Finally, the shutter can be closed for protecting the operation zone. The whole procedure can be carried out with one hand, whereby it is possible to make a personal measurement e.g. from the other hand or even the same hand that is carrying the device. The preparing of the measurement devices for use can carried out independently of the shutter as well, for example with separate switches after opening the shutter.

A typical application is the measurement of blood sugar, in which a portable measurement device is taken,
the shutter of the measurement device is moved from the first position to the second, whereby the operation zone of the measurement device and thereby also the measurement area of a new sensor strip is exposed (and typically also the piercing means is cocked), the piercing means is released in the vicinity of skin for bringing out blood (or tissue fluid), blood (or tissue fluid) is conveyed to the measurement area for carrying out the measurement, the sensor strip is removed from the device the shutter is closed.

The above described embodiments are exemplary and they can be freely combined and modified within the inventive idea disclosed in the appended claims. The claims are to be interpreted in their full scope, taking equivalence interpretation into consideration.

While the present invention has been illustrated and described with respect to a particular embodiment thereof, it should be appreciated by those of ordinary skill in the art that various modifications to this invention may be made without departing from the spirit and scope of the present invention.

What is claimed is:

1. A method for carrying out a health monitoring measurement using a portable health monitoring device, the device comprising:
   a first shutter;
   a second shutter; and
   a body having a first opening, a space within the body containing a plurality of sensor elements, a second opening and a piercing means,
   wherein the space within the body containing a plurality of sensor elements communicates with the first opening, and the piercing means is arranged to extend out from the second opening,
   wherein the method comprises the steps of:
   operating the first shutter to expose the first opening through which at least one of the sensor elements of the plurality of sensor elements can be accessed;
   operating the second shutter to expose the second opening and the piercing means;
   operating the piercing means to pierce a layer of skin at a sampling location; and
   obtaining a sample from the sampling location using the at least one of the sensor elements.

2. The method according to claim 1, wherein the step of operating the first shutter brings at least one sensor element into an operating position.

3. The method according to claim 2, wherein the step of operating the second shutter cocks the piercing means and brings the piercing means into the operating position.

4. A device for performing a health monitoring measurement on the blood of a subject comprising:
   a body having a first opening, a second opening, a space within the body containing a plurality of sensor strips and a piercing means, the space within the body containing a plurality of sensor strips communicating with the first opening and the piercing means arranged to extend out from the second opening; and
   a shutter means having a first shutter for covering the first opening and a second shutter for covering the second opening,
   wherein an operation of the first shutter exposes a first portion of the body containing the first opening and at least one of the plurality of sensor strips, and wherein an operation of the second shutter exposes a second portion of the body containing the second opening and the piercing means
   whereby the piercing means can pierce the skin of the subject to obtain a blood sample which can then be applied to the at least one sensor strip.

5. The device according to claim 4, wherein the operation of the first shutter brings a test strip into an operating position.

6. The device according to claim 5, wherein the operation of the second shutter cocks the piercing means and brings the piercing means into the operating position.

7. The device according to claim 4, wherein the piercing means is spring-loaded within the body.

8. The device of claim 7 wherein the shutter means consists of the first shutter and the second shutter and wherein the first shutter and the second shutter slide independently of each other in relation to the body.

9. The device according to claim 4, wherein the first shutter has a first position covering the first opening and a second position exposing the first opening, and wherein the operation of the first shutter moves the first shutter from the first position to the second position.

10. The device according to claim 4, wherein the operation of the first shutter and the operation of the second shutter occur simultaneously upon an operation of the shutter means.

11. The device according to claim 4, wherein the first shutter and the second shutter may be operated independently.

12. A health monitoring device comprising:
- a body having a first opening and a housing containing a plurality of sensor elements, the housing communicating with the first opening such that at least one sensor element of the plurality of sensor elements may be brought out of the said first opening;
- a lancet device attached to the body and having a second opening in the lancet device separate from the first opening in the body and a piercing means arranged to extend out from the second opening; and
- a shutter means for covering at least one of the first opening and the second opening,
- wherein the shutter means comprises a first shutter for covering the first opening and a second shutter for covering the second opening.

13. The device according to claim 12, further comprising a protective cover over the lancet device.

14. The device according to claim 12 wherein the at least one of the first shutter and second shutter are pivotally fastened to the body.

* * * * *